US012685814B2

(12) United States Patent
Lagorgette et al.

(10) Patent No.: US 12,685,814 B2
(45) Date of Patent: Jul. 21, 2026

(54) DRUG DELIVERY DEVICE

(71) Applicant: SENSILE MEDICAL AG, Olten (CH)

(72) Inventors: Pascal Lagorgette, Bienne (CH);
Fabian Bürli, Stüsslingen (CH)

(73) Assignee: SENSILE MEDICAL AG, Olten (CH)

( * ) Notice: Subject to any disclaimer, the term of this patent is extended or adjusted under 35 U.S.C. 154(b) by 460 days.

(21) Appl. No.: 18/460,722

(22) Filed: Sep. 5, 2023

(65) Prior Publication Data

US 2024/0082485 A1 Mar. 14, 2024

(30) Foreign Application Priority Data

Sep. 9, 2022 (EP) ..................................... 22194978

(51) Int. Cl.
*A61M 5/142* (2006.01)

(52) U.S. Cl.
CPC .... *A61M 5/14248* (2013.01); *A61M 5/14244* (2013.01); *A61M 2005/14268* (2013.01)

(58) Field of Classification Search
CPC .......... A61M 5/14248; A61M 5/14244; A61M 2005/14268
See application file for complete search history.

(56) References Cited

U.S. PATENT DOCUMENTS

| | | | |
|---|---|---|---|
| 7,726,955 B2 | 6/2010 | Ryser et al. | |
| 8,282,366 B2 | 10/2012 | Hilber et al. | |
| 8,382,700 B2 | 2/2013 | Straessler et al. | |
| 8,957,674 B2 | 2/2015 | Genoud et al. | |

| | | | |
|---|---|---|---|
| 9,222,470 B2 | 12/2015 | Genoud et al. | |
| 9,302,285 B2 | 4/2016 | Marbet et al. | |
| 9,662,621 B2 | 5/2017 | Beyer et al. | |
| 10,076,605 B2 | 9/2018 | Marbet et al. | |
| 10,143,798 B2 | 12/2018 | Marbet et al. | |
| 10,632,249 B2 | 4/2020 | Marbet et al. | |

(Continued)

FOREIGN PATENT DOCUMENTS

| | | | | |
|---|---|---|---|---|
| EP | 3574941 A1 * | 12/2019 | ........ | A61M 5/14248 |
| EP | 3 862 037 | 8/2021 | | |
| WO | WO 2015/015379 | 2/2015 | | |

OTHER PUBLICATIONS

Extended European Search Report for Application No. EP 22194978. 7, Feb. 20, 2023, pp. 1-8.

*Primary Examiner* — Edelmira Bosques
(74) *Attorney, Agent, or Firm* — SALIWANCHIK, LLOYD & EISENSCHENK

(57) ABSTRACT

This disclosure provides a drug delivery device (1) comprising a housing (2), a delivery unit (3), a drive unit (4) and a pumping system, the delivery unit comprising a subcutaneous delivery system (6) and a needle actuator system (7), the subcutaneous delivery system comprising a slidable needle support (10) and an injection needle mounted to the slidable needle support, the needle support movable with respect to the housing (2) from a retracted position where the needle is mounted within the housing, to an extended position where the needle projects through a skin contact wall (48) of the housing for subcutaneous delivery, the needle actuator mechanism comprising an actuation disc (12) rotatably mounted to a housing wall portion (38) within the housing (2) configured to displace the slidable needle support from the retracted position to the extended position by rotation of the actuation disc.

15 Claims, 8 Drawing Sheets

(56)                    References Cited

U.S. PATENT DOCUMENTS

| | | | |
|---|---|---|---|
| 10,954,928 | B2 | 3/2021 | Burli et al. |
| 11,009,018 | B2 | 5/2021 | Wyss et al. |
| 11,009,026 | B2 | 5/2021 | Girschweiler et al. |
| 11,022,107 | B2 | 6/2021 | Brandt et al. |
| 11,160,922 | B2 | 11/2021 | Just |
| 11,612,687 | B2 | 3/2023 | Marbet |
| 11,744,940 | B2 | 9/2023 | Wieser et al. |
| 2009/0030382 | A1 | 1/2009 | Brandt et al. |
| 2010/0241063 | A1 | 9/2010 | Straessler et al. |
| 2012/0046651 | A1 | 2/2012 | Beyer et al. |
| 2014/0231549 | A1 | 8/2014 | Thiemer et al. |
| 2022/0031940 | A1 | 2/2022 | Hulliger et al. |
| 2023/0398289 | A1 | 12/2023 | Wieser et al. |
| 2024/0033422 | A1 | 2/2024 | Büchi et al. |
| 2024/0033423 | A1 | 2/2024 | Muller et al. |
| 2024/0066541 | A1 | 2/2024 | Perrier et al. |
| 2024/0082486 | A1 | 3/2024 | Lagorgette et al. |
| 2024/0091460 | A1 | 3/2024 | Burli et al. |
| 2024/0157045 | A1 | 5/2024 | Kostal et al. |
| 2024/0165325 | A1 | 5/2024 | Burli |
| 2024/0173473 | A1 | 5/2024 | Burli |
| 2024/0175431 | A1 | 5/2024 | Mueller |
| 2024/0181153 | A1 | 6/2024 | Kostal et al. |
| 2024/0226425 | A9 | 7/2024 | Burli et al. |

* cited by examiner

DRUG DELIVERY DEVICE

TECHNICAL FIELD

This invention relates to a drug delivery device for subcutaneous administration of a liquid drug, for instance in the form of a patch device.

DESCRIPTION OF RELATED ART

Drug delivery devices in the form of a patch device for mounting on a patient's skin for subcutaneous delivery of liquid drug are known. It is known to provide drug delivery devices in the form of a patch device with a single use disposable unit assembled to a reusable unit containing drive and control electronics, or as a single unit disposable device incorporating all components and functions.

The reliability, safety, compactness and ease of use of drug delivery devices worn by a patient is important. For disposable components, the amount of parts and consequently cost of the disposable device is also an important consideration.

For safety of use of the drug delivery device, it is also important to ensure that it may only be actuated when attached to a patient's skin, that it remains sterile until administration of the drug, and that after use and removal the disposable portion of the device cannot be reused or harm someone.

In known drug delivery devices provided as patch devices that are placed against a patient's skin and held by an adhesive, an injection needle is actuated upon activation of the device for the sub-cutaneous delivery of the liquid medication.

There is need to reduce the complexity of mechanisms operated automatically in a drug delivery device to increase reliability and decrease costs, and further to increase the capacity of the medical device.

SUMMARY OF THE INVENTION

In view of the foregoing, it is an object of the invention to provide a drug delivery device with a needle actuation system that is reliable, compact, and safe.

It is advantageous to provide a drug delivery device with a needle actuation system that is economical to produce.

It is advantageous to provide a drug delivery device that is easy to operate.

Objects of the invention have been achieved by providing the drug delivery device according to claim 1. Dependent claims set forth various advantageous embodiments of the invention.

Disclosed herein is a drug delivery device comprising a housing, a delivery unit, a drive unit and a pumping system, the delivery unit comprising a subcutaneous delivery system and a needle actuator system, the subcutaneous delivery system comprising a slidable needle support and an injection needle mounted to the slidable needle support, the needle support movable with respect to the housing from a retracted position where the needle is mounted within the housing, to an extended position where the needle projects through a skin contact wall of the housing for subcutaneous delivery, the needle actuator mechanism comprising an actuation disc rotatably mounted to a housing wall portion within the housing configured to displace the slidable needle support from the retracted position to the extended position by rotation of the actuation disc. The drug delivery device further comprises a rotary drive shaft or stub comprising a coupling interface, the actuation disc comprising a complementary coupling interface engageable with the coupling interface of the rotary drive shaft or stub, the drug delivery device further comprising a motor coupled to the rotary drive shaft or stub.

The needle actuator mechanism further comprises a drive decoupling mechanism comprising a cam arrangement between the actuation disc and the housing wall portion and a spring, the spring and cam arrangement configured to effect an axial displacement of the actuation disc during rotation of the actuation disc causing displacement of the slidable needle support from the retracted to the extended position, the axial displacement causing a decoupling of the rotor drive shaft or stub coupling interface from the coupling interface of the actuation disc.

In an advantageous embodiment, the drive decoupling mechanism comprises a spring engagement flange or shoulder connected to the actuation disc via a connection portion extending through an orifice in the housing wall portion, the spring positioned in a prestressed manner between the spring engagement flange and a side of the housing wall portion opposite a side where the actuation disc is positioned.

In an advantageous embodiment, the spring is mounted on a rear side of the housing wall portion and the actuation disc is mounted on a front side of the housing wall portion.

In an advantageous embodiment, the cam arrangement is positioned between a rear side of the actuation disc and a front side of the housing wall portion, the drive coupling interface on the actuation disc being mounted on a front side of the actuation disc.

In an advantageous embodiment, the cam arrangement comprises a cam track on one of the actuation disc and front side of the housing wall portion and a cam pin on the other of the actuation disc and front side of the housing wall portion.

In an advantageous embodiment, the cam arrangement comprises a cam track having a slope at an inclination angle slope angle $\beta$ relative to a plane orthogonal to the direction of displacement of the actuation disc that is greater than the coefficient of friction of the cam arrangement such that the axial biasing of the spring causes the actuation disc to rotate to the fully extended position.

In an advantageous embodiment, the needle actuator mechanism comprises a pivoting actuation lever having a pivot portion mounted pivotally to the housing wall portion and a lever arm portion extending from the pivot portion engageable with the actuation disc, the lever arm portion comprising a needle support coupling engaging a complementary coupling of the needle support for displacing the needle support from the retracted to the extended position.

In an advantageous embodiment, the actuation disc comprises a lever engagement member in the form of an indent configured to engage a tip of the lever arm portion.

In an advantageous embodiment, the drive decoupling mechanism comprises a spring engagement member in the form of a button comprising the spring engagement flange or shoulder assembled to the actuation disc through an orifice in the housing wall portion.

In an advantageous embodiment, the rotary drive shaft or stub is connected to a motor of the drive unit, said motor also coupled to a pumping system of the drug delivery device for pumping of the liquid drug from a drug container to the needle.

In an advantageous embodiment, the rotary drive shaft or stub comprises gear teeth for coupling to a rotor of the motor or pumping system.

In an advantageous embodiment, the coupling interface between the rotary drive shaft or stub and the actuation disc comprises a key and slot arrangement.

In an embodiment, the delivery unit and drive unit are formed as separate parts that may be assembled together, the delivery unit being a disposable single use part and the drive unit a reusable part.

In an alternative embodiment, the delivery unit and drive unit are mounted in a housing as a disposable single part.

In an embodiment, the pumping system comprises a pneumatic pumping system applying pressure on a drug container mounted in the drug delivery device.

In an advantageous embodiment, the drug container is in the form of a cartridge with a plunger.

BRIEF DESCRIPTION OF THE DRAWINGS

Further objects and advantageous features of the invention will be apparent from the claims, from the detailed description, and annexed drawings, in which:

FIG. 2b is an exploded perspective view of the device of FIG. 2a;

FIG. 3a illustrates a view towards a drive coupling side of the device;

FIG. 3b illustrates a cross-section through line B of FIG. 3a;

FIG. 3c illustrates a perspective view of the device of FIG. 3a towards a back end;

FIG. 3d illustrates an enlarged of view of a portion denotated D of FIG. 3c;

FIGS. 4a-4d show the needle actuation mechanism in an intermediate position between a fully retracted position as shown in FIGS. 3a-3d and the fully extended position as shown in FIGS. 7a-7d, FIGS. 5a-5d showing a subsequent position with the actuation mechanism approaching the fully extended position;

FIGS. 6a-6d show a subsequent position from FIGS. 5a-5d in which the actuation mechanism is being decoupled;

FIGS. 7a-7d show the actuation mechanism fully decoupled and the needle in the fully extended position corresponding to the position during drug delivery.

DETAILED DESCRIPTION OF EXEMPLARY EMBODIMENTS

Figures 1A, 1B, 1C:
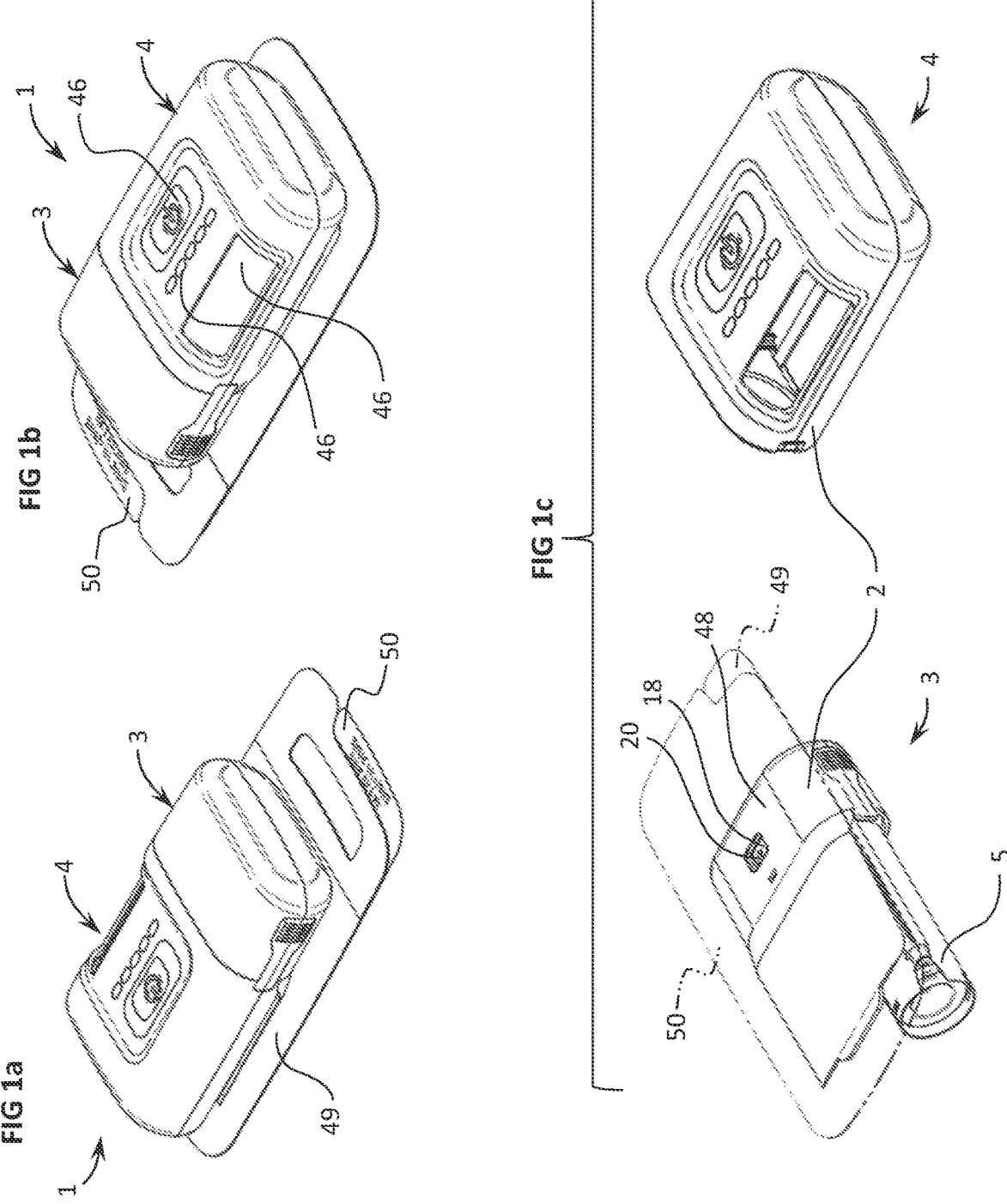
FIGS. 1a and 1b are a perspective views from left and right sides of a drug delivery device according to an embodiment of the invention.
FIG. 1c is a perspective view of the drug delivery device of FIGS. 1a and 1 b with delivery and drive units separated.
Figure 2A:
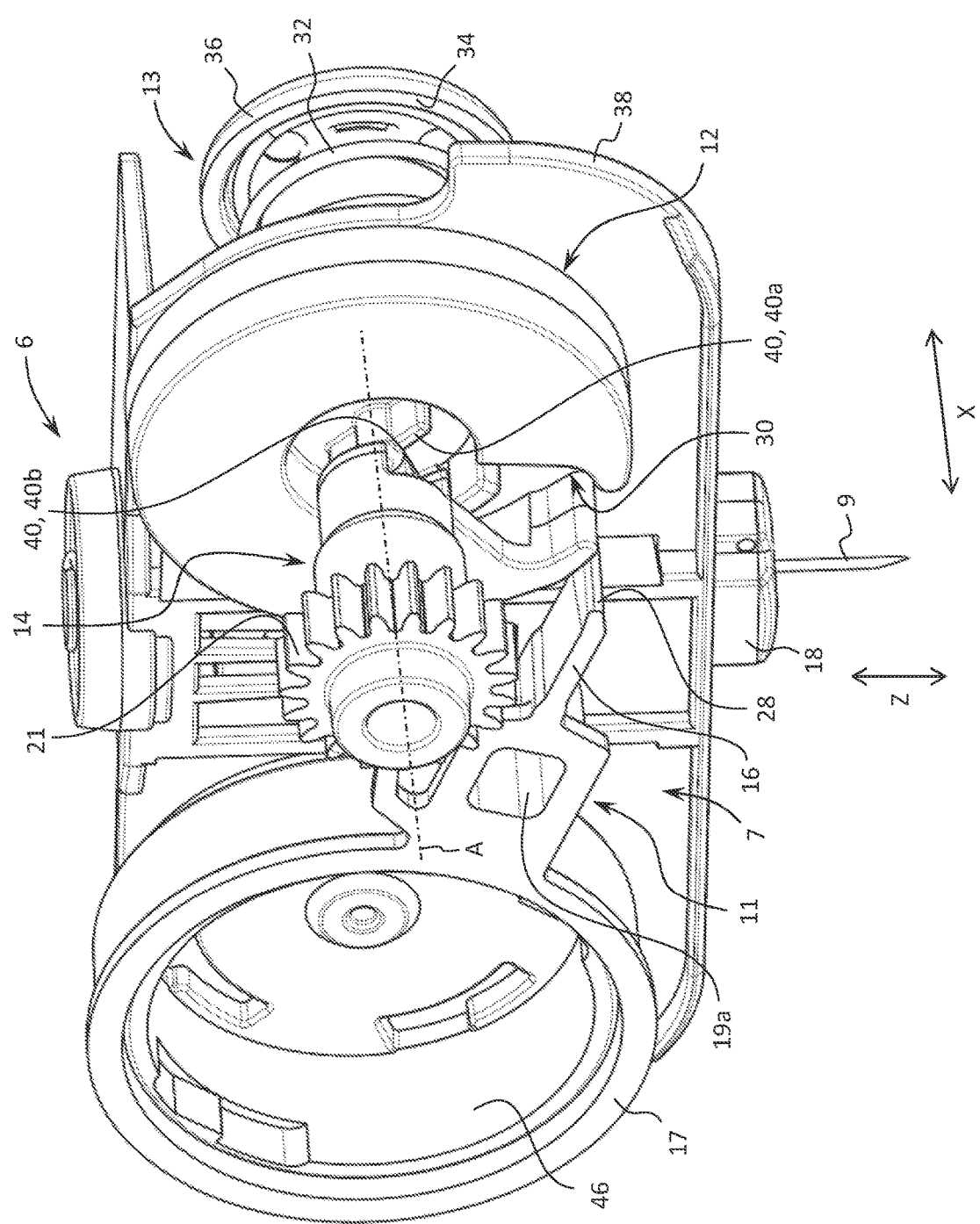
FIG. 2a is a perspective view of a portion of a delivery unit of a drug delivery device according to an embodiment of the invention; in particular illustrating a subcutaneous delivery system and needle actuator system of the device.
Figure 2B:
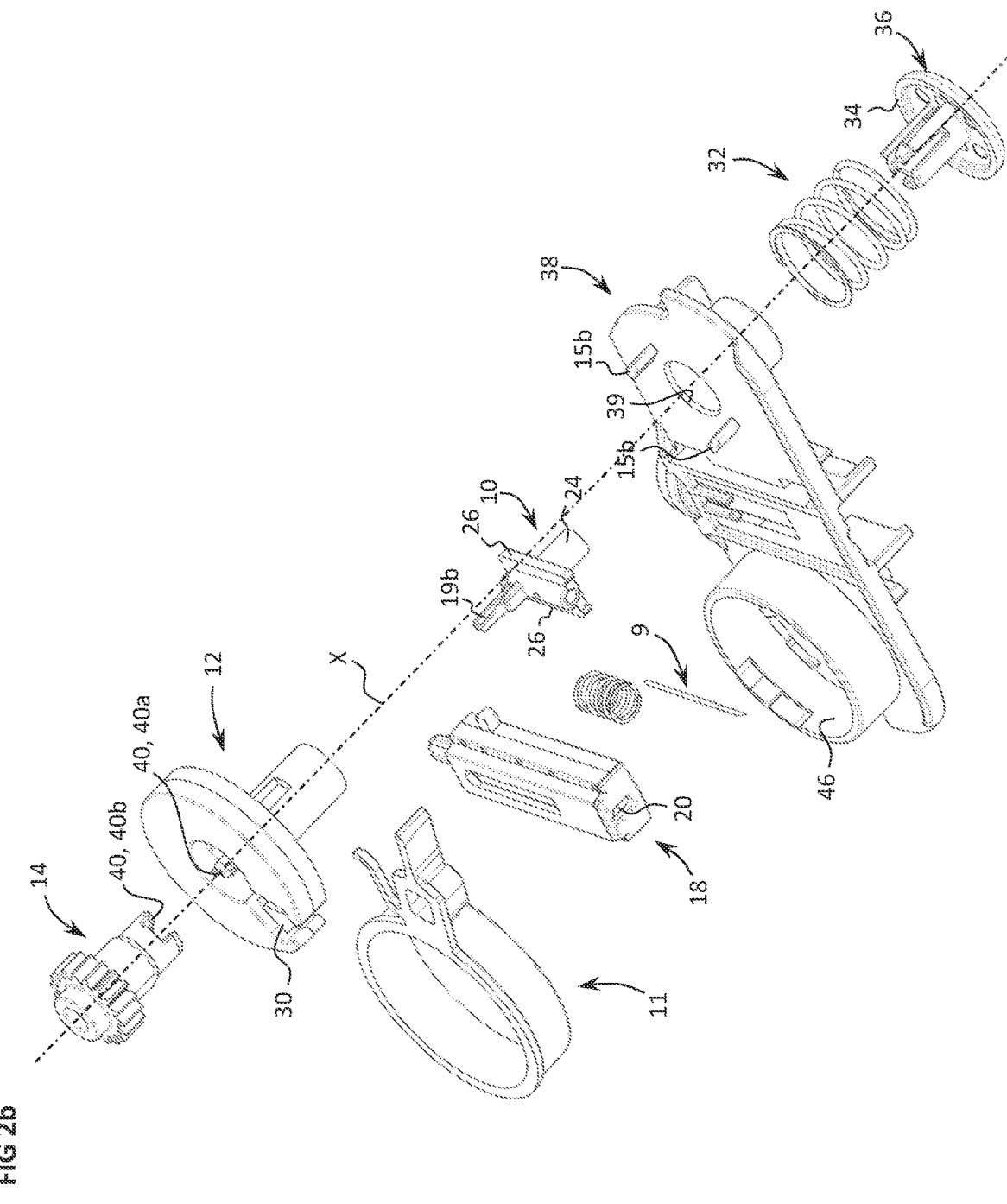
Figures 3A, 3B, 3C, 3D:
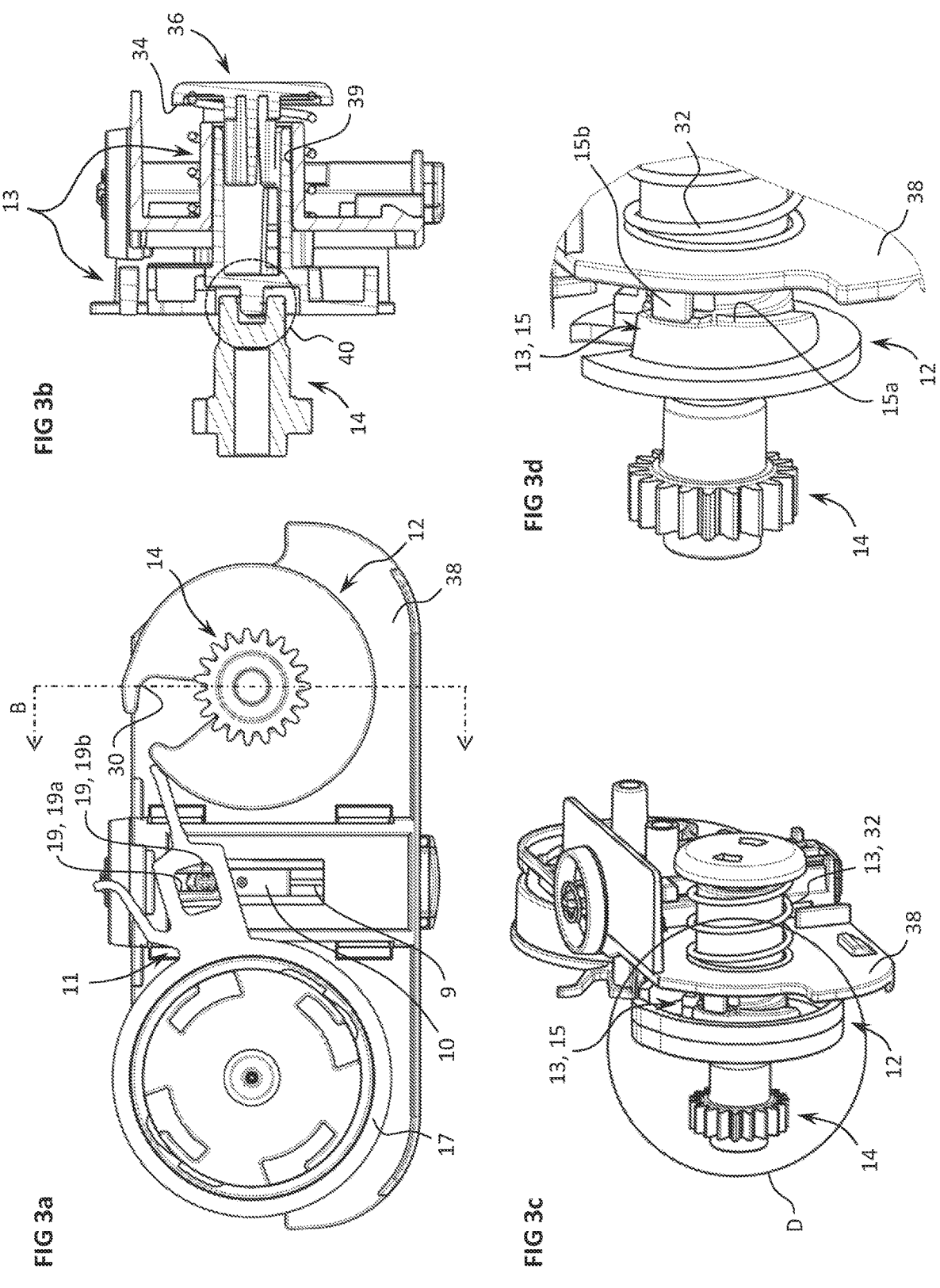
FIGS. 3a-3d show views of the device of FIG. 2a in an initial state prior to use of the drug delivery device, whereby.

Referring to the figures, a drug delivery device 1 according to embodiments of the invention comprise a housing 2, a delivery unit 3, and a drive unit 4, the delivery unit 3 and the drive unit 4 being assembled within the housing 2. The housing 2 may be made of two or more parts allowing assembly of the delivery unit 3, drive unit 4 and any other components within the housing 2.

In the illustrated embodiments, the drug delivery device 1 for subcutaneous administration of a liquid drug (medicament) comprises a disposable portion formed by the delivery unit 3 that may be assembled to a reusable portion formed by the drive unit, which includes electronics and a power supply. The delivery unit 3 is mounted in a first housing wall portion of the drug delivery device and the drive unit 4 in a separable second housing wall portion such that the drive unit 4 can be reused with subsequent delivery units.

Although the embodiments shown in the figures concern a two-part drug delivery device with disposable and reusable units, within the scope of the invention for various aspects described herein, the drug delivery device may be a single use disposable unit. The administration may occur in a single dose over a short period of time, typically less than 1 hour, for instance around 30 minutes or less. A single use disposable drug delivery device may also be used for subcutaneous injection of a liquid drug over an extended period of time from a few hours to a few days. Depending on the volume of the drug to be injected, the drug delivery device may also be configured to inject the liquid drug within a few minutes.

The drug delivery device includes a user interface 46 that may include one or more buttons for actuating the drug delivery device 1, light and/or sound status indicators, and optionally a screen or other display for presenting information to an operator of the device.

Drug delivery devices according to embodiments of the invention may advantageously be configured as a patch device for mounting on a patient's skin. An adhesive layer 49 may be provided on an outer surface of a skin contact wall 48 of the housing 2 covered by a protective film 50 that may be peeled off the adhesive layer 49 prior to placing the adhesive layer on the patient's skin at the site of injection. A needle orifice 20 on the skin contact side is covered by the protective film 50 prior to use, and allows a transcutaneous injection needle 9 to extend therethrough and pierce the patent's skin upon activation of the drug delivery device 1.

The delivery unit 3 comprises a drug container 5, for instance a drug cartridge, containing a liquid drug, a subcutaneous delivery system 6 including an injection needle 9 for channeling the liquid drug to a patient subcutaneously, and a needle actuation mechanism 7 configured to move the injection needle from a retracted position prior to use, to an extended position for subcutaneous drug delivery.

The drug delivery device further includes a pumping system (not shown) that causes liquid from the drug container to be pumped to the injection needle 9 once the drug delivery device has been activated.

In an embodiment, the pumping system may be mounted in the drive unit and apply pressure on a plunger of the drug container to push liquid out of the drug container into the subcutaneous delivery system by positive pressure. Various per se known means for applying pressure on a drug container plunger may be employed.

In an advantageous embodiment the pumping system may comprise a pneumatic pumping system as described in patent application PCT/EP2022/055835.

The drive unit 4 may have additional functions such as processing sensing signals, and transmitting and receiving data from an external device via a wireless communication link, for instance using Bluetooth.

The subcutaneous delivery system 6 comprises a slidable needle support 10 which is slidably mounted within the housing 2, the needle 9 being mounted on the needle support 10 and movable with the needle support 10 from a fully retracted position within the housing of the delivery unit 3, to a fully extended position during drug administration.

The slidable needle support comprises a fluidic channel extending therein from the needle to a supply tube connection portion 24 that couples to a drug supply tube (not shown). The drug supply tube may advantageously be in the form of a supple tube allowing the sliding movement of the needle support from the retracted to the extended positions, the tube being connected to a drug supply (i.e. the drug container, for instance via a septum needle (not shown) that pierces through a septum of a drug cartridge).

The slidable needle support comprises one or more guides 26, for instance in the form of rails that engage complementary guides of a housing wall portion 38 to slidably guide the needle support during actuation thereof by the needle actuator mechanism 7.

The needle actuation mechanism 7 comprises a rotatable actuation disc 12 rotatably mounted about an axis X that is orthogonal to a sliding displacement axis Z of the needle 9, the actuation disc 12 being couplable to a rotary drive shaft or stub 14. The rotary drive shaft or stub 14 is coupled to a motor (not shown) mounted in the drive unit 4. The motor may be a motor of the drive unit that is dedicated for the needle actuation mechanism, or may be a motor that serves both for the needle actuation mechanism and also to drive a pumping system of the drug delivery device that forces the liquid to flow from the drug container to the needle.

In preferred embodiments, the motor comprises a rotary motor that drives a rotor of a pump engine having a configuration as described in WO 2015015379 or in PCT/EP2022/055835.

In this preferred configuration, the displacement of the needle from the retracted position within the housing to the extended position for drug delivery where the needle pierces through a patient's skin may only occur when the drug delivery device is actuated and the liquid pumping is started. This increases safety by ensuring that the needle is only actuated when the drug delivery device is placed against the patient's skin and the drug pumping cycle begins. Moreover, it allows to use a single motor for both the needle actuation and the drug pumping.

As noted above, the pumping of the drug may be effected by various mechanisms that press on a plunger of a drug cartridge or other movable wall of a drug container, for instance a supple drug container, for instance using a pneumatic pump system as described in the aforementioned application PCT/EP2022/055835, or that draws liquid from the drug container by suction, for instance as described in WO 2015015379.

The pumping system may also include other per se well known pumping systems, for instance the motor may drive a linear nut and screw system that presses on the plunger.

In all the aforementioned configurations, the motor may be coupled to both the pump system drive and to the rotary drive shaft or stub 14 for actuation of displacement of the needle from the retracted to the fully extended position.

In the illustrated embodiment, the needle actuation mechanism further comprises an actuation lever 11 pivotally mounted to the housing wall portion 38. The actuation lever 11 comprises a pivot portion 17 in the form of a support ring that is mounted around a shroud 46 that may serve to receive a cap end of a drug cartridge therein. The pivot portion may however be coupled to a pivot axis or orifice formed in the housing wall portion 38 independent of any shroud for receiving a drug cartridge.

The actuation lever 11 further comprises a lever arm portion 16 extending from the pivot portion 17 to a tip 28. The lever arm portion comprises a needle support coupling 19 configured to engage a corresponding coupling provided on the slidable needle support 10 such that when the actuation lever is pivoted from a first position to a second position, the slidable needle support is moved from a first retracted position to a second extended position by engagement with the actuation lever 11.

In the illustrated embodiment, the needle support coupling 19 comprises a slot 19a formed in the lever arm portion 16 and a pin 19b extending from the housing, but the skilled person will appreciate that such arrangement may be inversed, for instance having a pin extending from the lever arm portion and a slot in the slidable needle support.

In the illustrated embodiment, the actuation disc comprises a lever engagement member 30 that engages the lever arm portion 16 of the actuation lever 11 upon rotation of the actuation disc 12. In the illustrated embodiment, the lever engagement member is formed as an indent in the actuation disc within which the tip 28 of the actuation lever is received, however the skilled person will appreciate that it would be possible to have, instead of an indent, a pin or other form of protuberance mounted at or near the periphery of the actuation disc that engages the actuation lever near the tip 28 such that when the actuation disc rotates (in the figures in the anti-clockwise direction), the protuberance engages the lever arm and makes it rotate in the opposite (in this case the clockwise) direction which thus causes the needle support housing to move from the retracted to extended positions.

Within the scope of the invention, it would however be possible to have the actuation disc 12 directly engage the slidable needle support 10 without the presence of the actuation lever 11. For instance, the actuation disc could have an arm or other form of extension that has a slot or pin engaging a complementary pin or slot on the slidable needle support. Such an arrangement is possible within the scope of the present invention because the actuation disc 12 decouples from the rotary drive shaft or stub 14 when the slidable needle support reaches the extended position as described in more detail below.

According to an aspect of the invention, the needle actuator mechanism 7 further comprises a drive decoupling mechanism 13 which is configured to ensure that the actuation disc 12 is coupled to the rotary drive shaft or stub 14 in the retracted position of the slidable needle support 10, and to decouple the actuation disc 12 from the rotary drive shaft or stub 14 when the slidable needle support 10 is in the extended position for drug delivery.

The drive decoupling mechanism 13 comprises a cam arrangement 15, 15a, 15b configured for axially displacing the actuation disc 12 relative to the housing wall portion 38 as a function of the angle of rotation of the actuation disc 12 relative to the housing wall portion 38.

In the illustrated embodiment, the cam arrangement comprises a cam track 15a arranged on an inner side of the actuation disc 12 opposite the drive coupling interface side, engaging a cam pin 15b extending from the housing wall portion 38. For reasons of stability, a pair of cams may be arranged diametrically opposed from the rotation axis X as illustrated. The skilled person will appreciate that it would of course be possible to invert the cam arrangement, namely to have the cam pins protruding from the actuation disc engaging the cam tracks on the housing wall portion. The term "pin" is not intended to mean specifically a pin-shape and may include any protuberant shape adapted to engage a cam track.

The cam track and pin are biased together by the force of a spring 32 of the drive decoupling mechanism 13.

In the illustrated embodiment, the spring 32 is provided on an opposite side of the housing wall portion 38 from the actuation disc and presses a spring engagement flange or shoulder 34 that is fixed to the actuation disc, thus pulling the actuation disc towards the front side of the housing wall portion 38.

The spring engagement flange 34 may be provided for instance in the form of a button 36 that may be clipped, welded or fixed by other means to the actuation disc 12. It would be understood that various other spring mechanisms or biasing mechanisms for ensuring that the complementary cam track 15a and pin 15b remain in contact, may be used. For instance, the spring may be integrally formed with a support member such as the button 36 (instead of being a separate assembled spring) or a spring element may act in traction instead of compression to pull the actuation disc against or towards the housing wall portion 38.

As best seen in FIGS. 3a to 3d, when the needle is in the retracted position, the cam arrangement 15, 15a, 15b defines an axial position of the actuation disc 12 such that the drive coupling interface 40a of the actuation disc 12 engages the complementary drive coupling interface 40b of the rotary drive shaft or stub 14.

In the illustrated embodiments, the drive coupling interface 40a is provided as a key slot and the actuator coupling interface 40b of the rotary drive shaft or stub as a complementary key that inserts into the key slot. However, the skilled person will understand that various inter-engaging teeth may be provided to ensure the coupling between the rotary drive shaft or stub 14 and the actuation disc 12, provided the coupling interface is axially relatively movable to allow decoupling when the axial position of the actuation disc is shifted from an engaged position to a disengaged position.

Figures 4A, 4B, 4C, 4D:
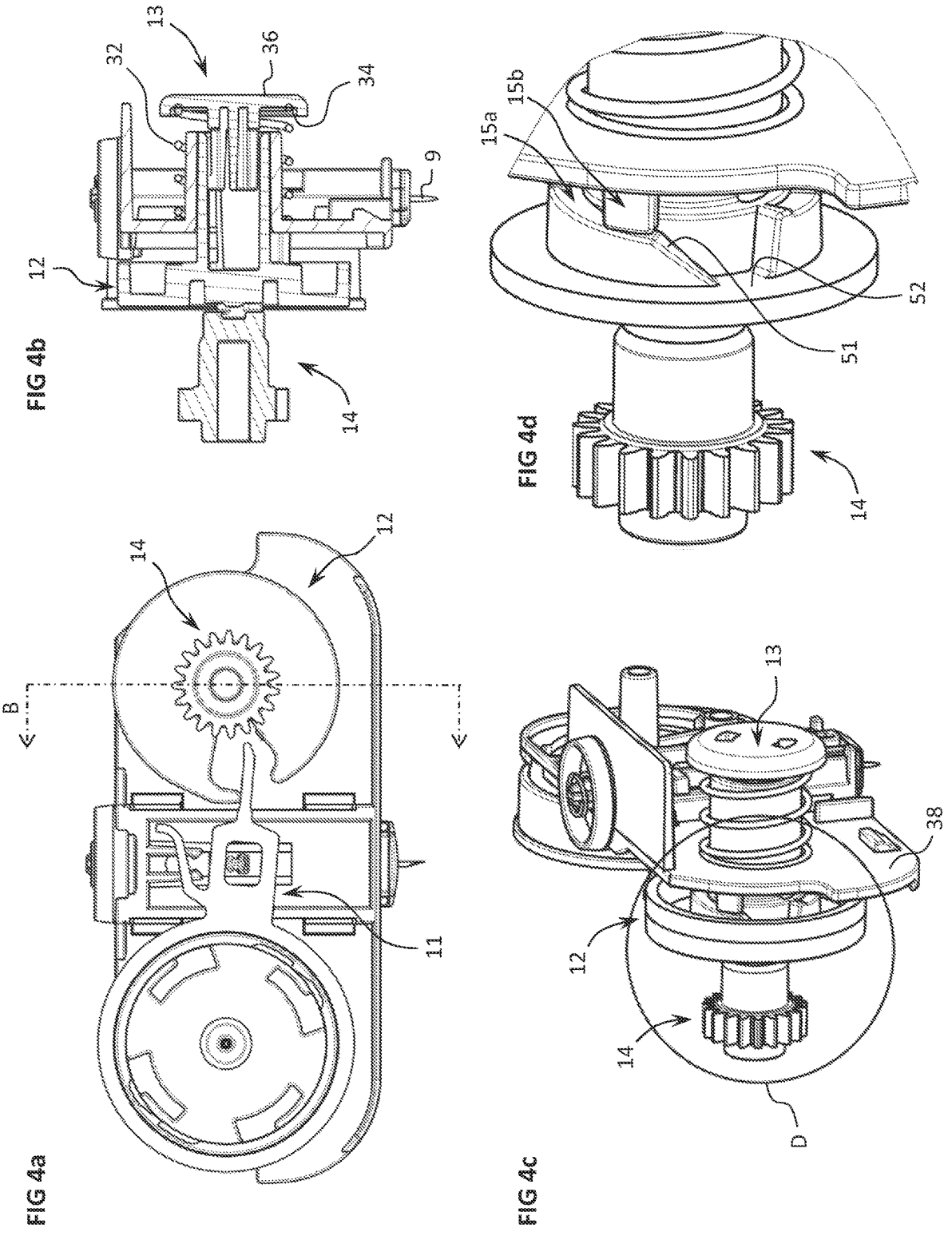
FIGS. 4a-4d, 5a-5d, 6a-6d and 7a-7d are similar to FIGS. 3a-3d except showing the device in different stages, the figures (a) to (d) being views that correspond to the FIGS. 3a to 3d, whereby.
Figures 5A, 5B, 5C, 5D:
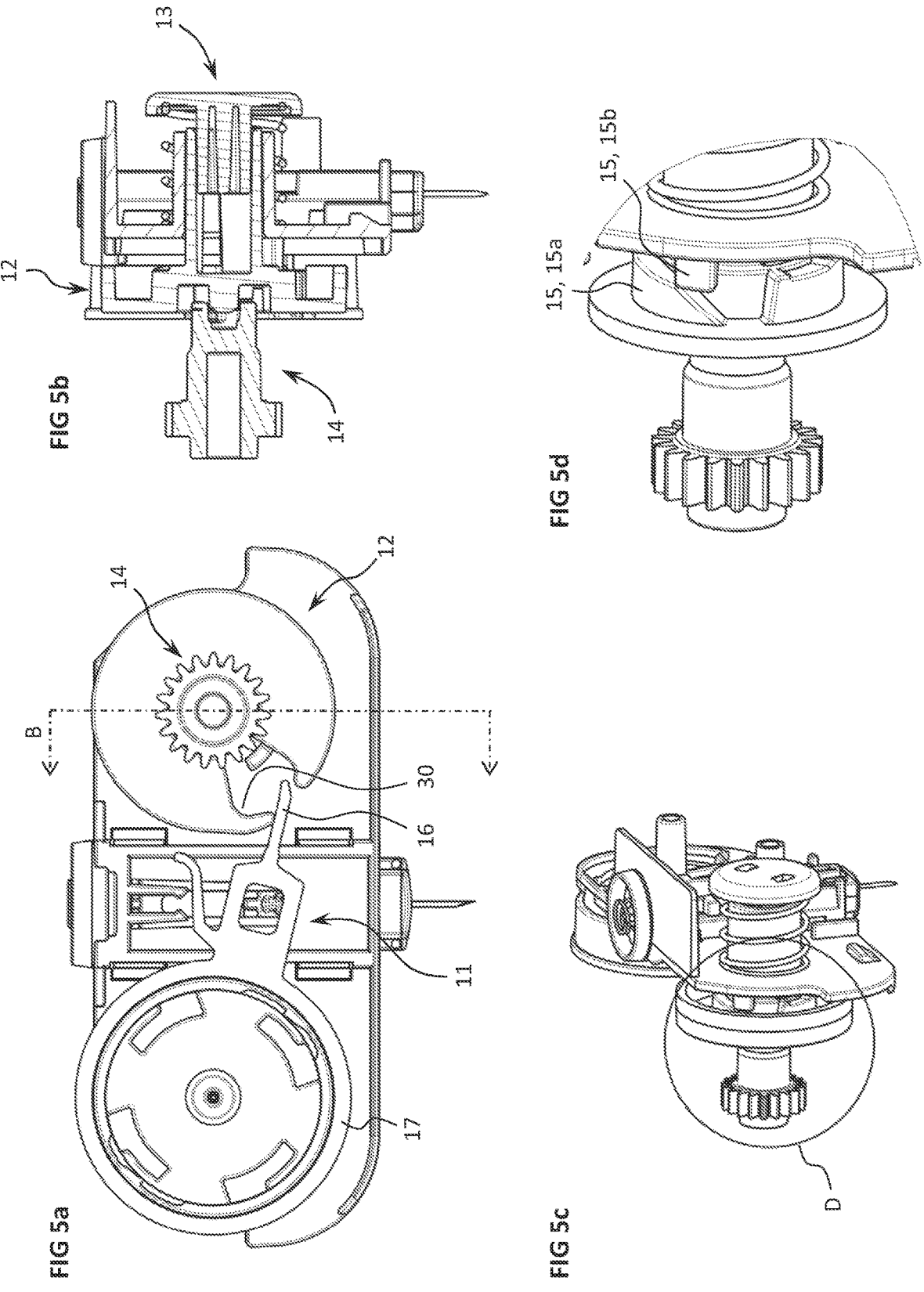
Figures 6A, 6B, 6C, 6D:
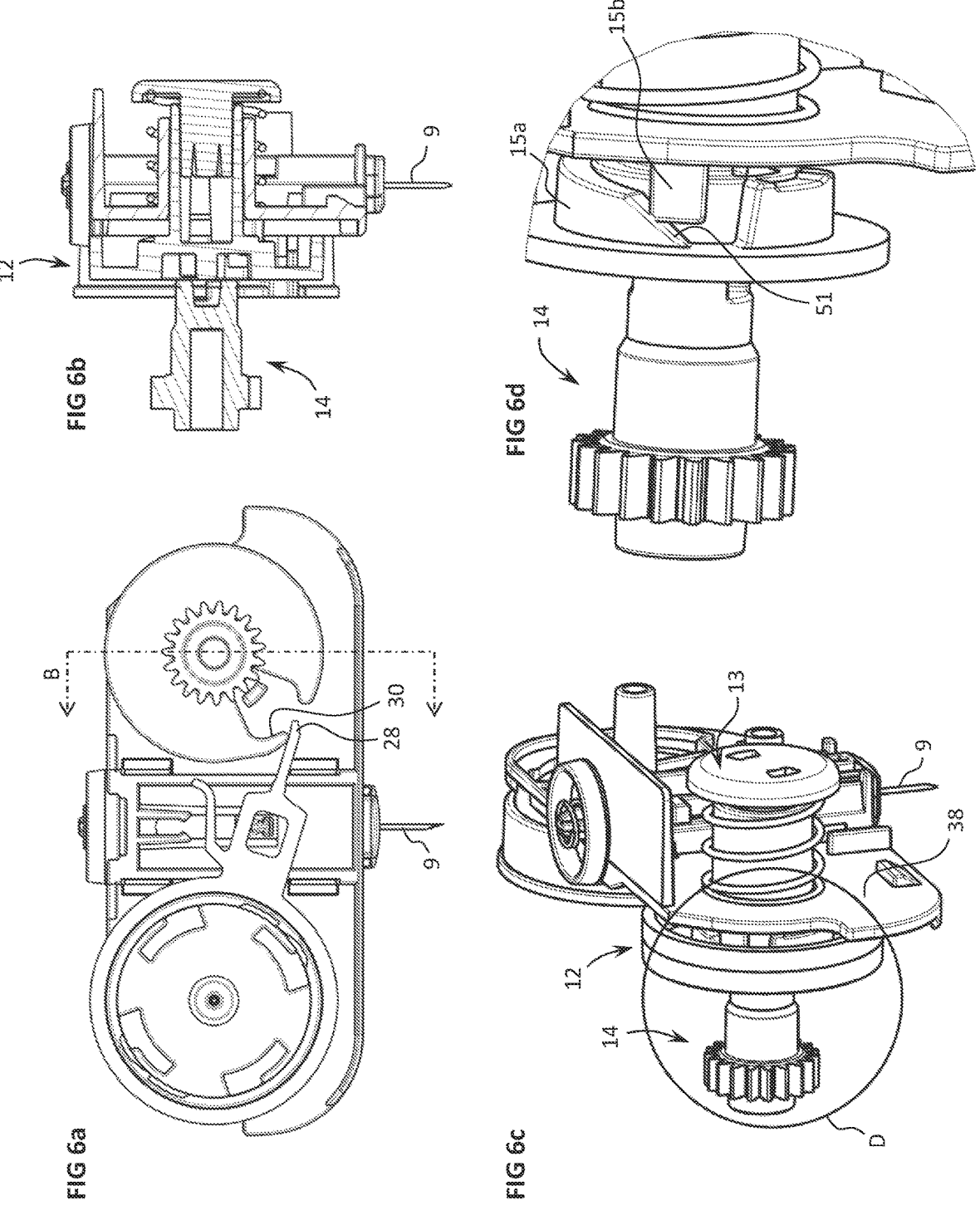
Figures 7A, 7B, 7C, 7D:
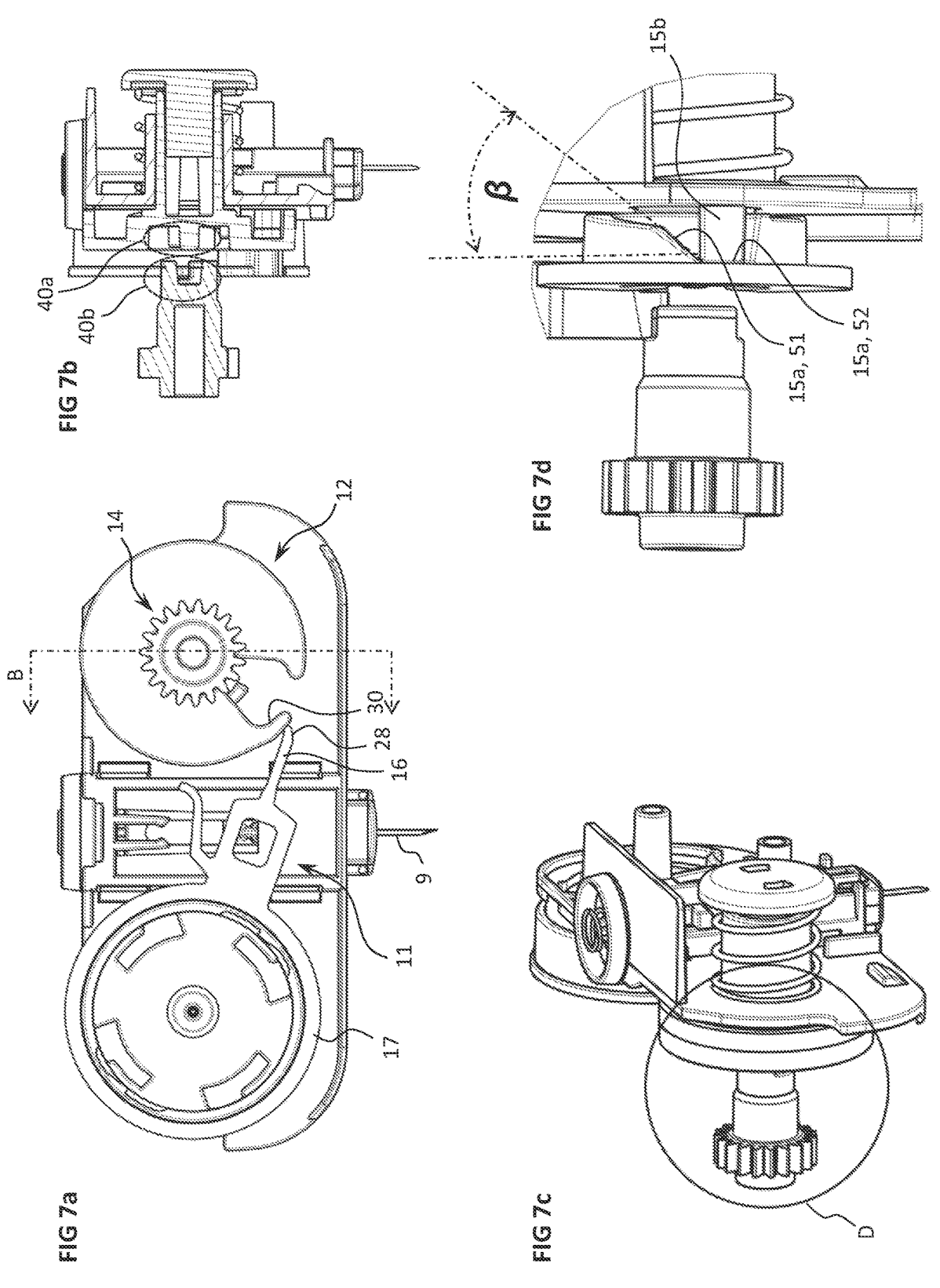

As best seen in FIGS. 3a to 3d, and in particular 3d, the cam pin 15b presses on the cam track 15a which has a high position defining an axial position of the actuation disc where it is furthest from the housing wall portion 38 and closest to the drive shaft or stub 14 such that the coupling interfaces 40a, 40b are engaged. Rotation of the actuation disc 12 from the retracted position shown in FIG. 3 through the intermediate positions shown in FIG. 4 to an almost fully extended position shown in FIG. 5 and a fully extended position shown in FIG. 6, causes the cam pin to travel relatively along the cam track, and when the rotation of the actuation disc 12 reaches the needle fully extended position, the cam arrangement causes an axial displacement of the actuation disc such that it disengages from the drive shaft or stub 14. The cam track and pin ensures that while the needle support is being displaced that the coupling interfaces 40a, 40b of the drive shaft or stub and actuation disc are engaged whereas when the fully extended position is approached, the cam arrangement allows an axial displacement of the actuation disc towards the housing wall portion 38 due to the biasing force of the spring 32 until the axial movement of the actuation disc causes the coupling interfaces 40a, 40b to fully disengage as illustrated in FIG. 7.

The cam track portion 51 adjacent the fully extended position portion 52 may be configured with a slope angle β (relative to the plane orthogonal to the axial axis X) that is sufficient to cause the actuation disc to continue rotating due to the biasing force of the spring 32 even in the absence between the coupling interfaces 40a, 40b. This ensures that the actuation disc completes the required angle of rotation for both fully extending the needle and fully disengaging the actuation disc from the rotary drive shaft or stub. The slope angle β is greater than a coefficient of friction between the cam track and cam pin and preferably less than 60° to ensure a certain rotation displacement associated to the axial displacement at the end of travel.

Advantageously, the decoupling mechanism according to embodiments of the invention allows the drive shaft or stub 14 to continue to rotate, for instance if it forms part of a motor that also drives the pumping system, without interference with the needle actuation mechanism, and at the same time also allowing the motor to be used for both the needle actuation at the beginning of the drug delivery process and for the pumping of the liquid that commences upon actuation of the needle and continuing thereafter.

LIST OF FEATURES

Drug delivery device 1
Housing 2
   Skin contact wall 48
      Needle shield orifice 20
   Adhesive layer 49
   Protective film 50
Delivery unit 3
   Drug container 5
   Subcutaneous delivery system 6
      Injection needle 9
      Slidable Needle support 10
         Actuator coupling 22
         Supply tube connection 24
         Guide 26
   Needle actuator mechanism 7
      Actuation lever 11
         Pivot portion 17
            Support ring
         Lever arm portion 18
            Needle support coupling 19
            Slot 19a
            Tip 28
      Actuation disc 12
         Lever engagement member 30
         Indent
         (Drive) coupling interface 40a
         Key
      Drive decoupling mechanism 13
         Spring 32
         Spring engagement flange/shoulder 34
            Button 36
         Cam arrangement 15, 15a, 15b
            Cam track 15a
            Cam pin 15b
      Housing wall portion 38
         Orifice 39
      Rotary Drive shaft/stub 14
         (Actuator) Coupling interface 40b
            slot
         Gear teeth 21
   Needle shield cover 16
Drive unit 4
   Electronic control system
   Power source (battery)
   User interface 46
Pumping system
   Pump engine
      Stator
      Rotor

The invention claimed is:

1. A drug delivery device comprising a housing, a delivery unit, a drive unit and a pumping system, the delivery unit comprising a subcutaneous delivery system and a needle actuator system, the subcutaneous delivery system comprising a slidable needle support and an injection needle mounted to the slidable needle support, the needle support movable with respect to the housing from a retracted position where the needle is mounted within the housing, to an extended position where the needle projects through a skin contact wall of the housing for subcutaneous delivery, the needle actuator system comprising an actuation disc rotatably mounted to a housing wall portion within the housing configured to displace the slidable needle support from the retracted position to the extended position by rotation of the actuation disc, the drug delivery device further comprising a rotary drive shaft or stub comprising a coupling interface, the actuation disc comprising a coupling interface engageable with the coupling interface of the rotary drive shaft or stub, the drug delivery device further comprising a motor coupled to the rotary drive shaft or stub, wherein the needle actuator system further comprises a drive decoupling mechanism comprising a cam arrangement between the actuation disc and the housing wall portion and a spring, the spring and cam arrangement configured to effect an axial displacement of the actuation disc during rotation of the actuation disc causing displacement of the slidable needle support from the retracted to the extended position, the axial displacement causing a decoupling of the rotor drive shaft or stub coupling interface from the coupling interface of the actuation disc.

2. The drug delivery device according to claim 1, wherein the drive decoupling mechanism comprises a spring engagement flange or shoulder connected to the actuation disc via a connection portion extending through an orifice in the housing wall portion, the spring positioned in a prestressed manner between the spring engagement flange and a side of the housing wall portion opposite a side where the actuation disc is positioned.

3. The drug delivery device according to claim 1, wherein the spring is mounted on a rear side of the housing wall portion and the actuation disc is mounted on a front side of the housing wall portion.

4. The drug delivery device according to claim 1, wherein the cam arrangement is positioned between a rear side of the actuation disc and a front side of the housing wall portion, the drive coupling interface on the actuation disc being mounted on a front side of the actuation disc.

5. The drug delivery device according to claim 1, wherein the cam arrangement comprises a cam track on one of the actuation disc and front side of the housing wall portion and a cam pin on the other of the actuation disc and front side of the housing wall portion.

6. The drug delivery device according to claim 1, wherein the cam arrangement comprises a cam track having a slope at an inclination angle slope angle $\beta$ relative to a plane orthogonal to the direction of displacement of the actuation disc that is greater than the coefficient of friction of the cam arrangement such that the axial biasing of the spring causes the actuation disc to rotate to the fully extended position.

7. The drug delivery device according to claim 1, wherein the needle actuator mechanism comprises a pivoting actuation lever having a pivot portion mounted pivotally to the housing wall portion and a lever arm portion extending from the pivot portion engageable with the actuation disc, the lever arm portion comprising a needle support coupling engaging a complementary coupling of the needle support for displacing the needle support from the retracted to the extended position.

8. The drug delivery device according to claim 7, wherein the actuation disc comprises a lever engagement member in the form of an indent configured to engage a tip (28) of the lever arm portion.

9. The drug delivery device according to claim 1, wherein the drive decoupling mechanism comprises a spring engagement member in the form of a button comprising the spring engagement flange or shoulder assembled to the actuation disc through an orifice in the housing wall portion.

10. The drug delivery device according to claim 1, wherein the motor coupled to the rotary drive shaft or stub is also coupled to a pumping system of the drug delivery device for pumping of the liquid drug from a drug container to the needle.

11. The drug delivery device according to claim 1, wherein the rotary drive shaft or stub comprises gear teeth for coupling to a rotor of the motor or pumping system.

12. The drug delivery device according to claim 1, wherein the coupling interface between the rotary drive shaft or stub and the actuation disc comprises a key and slot arrangement.

13. The drug delivery device according to claim 1, wherein the delivery unit and drive unit are formed as separate parts that may be assembled together, the delivery unit being a disposable single use part and the drive unit a reusable part.

14. The drug delivery device according to claim 1, wherein the pumping system comprises a pneumatic pumping system applying pressure on a drug container mounted in the drug delivery device.

15. The drug delivery device according to claim 14, wherein the drug container is in the form of a cartridge with a plunger.

* * * * *